(12) United States Patent
Kim et al.

(10) Patent No.: US 11,576,995 B2
(45) Date of Patent: Feb. 14, 2023

(54) METHOD FOR MANUFACTURING PHOTOCATALYTIC FILTER FOR AIR PURIFICATION

(71) Applicants: Samsung Electronics Co., Ltd., Gyeonggi-do (KR); POSTECH ACADEMY-INDUSTRY FOUNDATION, Gyeongsangbuk-do (KR)

(72) Inventors: Jee-yeon Kim, Seoul (KR); Wonyong Choi, Gyeongsangbuk-do (KR); Seunghyun Weon, Seoul (KR); Sae-mi Kim, Seoul (KR); Hee-jin Park, Seoul (KR)

(73) Assignees: Samsung Electronics Co., Ltd; Postech Academy-Industry Foundation

( * ) Notice: Subject to any disclaimer, the term of this patent is extended or adjusted under 35 U.S.C. 154(b) by 194 days.

(21) Appl. No.: 16/771,161

(22) PCT Filed: Jul. 31, 2018

(86) PCT No.: PCT/KR2018/008679
§ 371 (c)(1),
(2) Date: Jun. 9, 2020

(87) PCT Pub. No.: WO2019/139209
PCT Pub. Date: Jul. 18, 2019

(65) Prior Publication Data
US 2021/0170061 A1    Jun. 10, 2021

(30) Foreign Application Priority Data

Jan. 9, 2018 (KR) .................. 10-2018-0002699

(51) Int. Cl.
*A61L 9/20* (2006.01)
*B01D 39/10* (2006.01)
(Continued)

(52) U.S. Cl.
CPC .............. *A61L 9/205* (2013.01); *B01D 39/10* (2013.01); *B01D 53/86* (2013.01); *C01G 23/053* (2013.01);
(Continued)

(58) Field of Classification Search
CPC ......... A61L 9/205; B01D 39/10; B01D 53/86; C01G 23/053
See application file for complete search history.

(56) References Cited

FOREIGN PATENT DOCUMENTS

| CN | 101717983 | 6/2010 |
|----|-----------|--------|
| CN | 102677123 | 9/2012 |

(Continued)

OTHER PUBLICATIONS

PCT/ISA/210 Search Report issued on PCT/KR2018/008679 pp. 5. (dated Jul. 18, 2019).
(Continued)

*Primary Examiner* — James A Fiorito
(74) *Attorney, Agent, or Firm* — The Farrell Law Firm, P.C.

(57) ABSTRACT

Disclosed is a method for manufacturing a photocatalytic filter for air purification. The present manufacturing method comprises the steps of: oxidizing a titanium metal to obtain a nanostructured titanium dioxide (TiO2); adding the nanostructured titanium dioxide to an acidic fluorine-containing solution to allow a reaction to occur therebetween for a predetermined period of time; and, after treatment in the acidic fluorine-containing solution, performing heat treatment on the nanostructured titanium dioxide.

8 Claims, 6 Drawing Sheets

(51) Int. Cl.
*B01D 53/86* (2006.01)
*C01G 23/053* (2006.01)
*B82Y 30/00* (2011.01)
*B82Y 40/00* (2011.01)

(52) U.S. Cl.
CPC ....... *A61L 2209/14* (2013.01); *B01D 2201/18* (2013.01); *B01D 2258/06* (2013.01); *B82Y 30/00* (2013.01); *B82Y 40/00* (2013.01); *C01P 2004/64* (2013.01)

(56) References Cited

FOREIGN PATENT DOCUMENTS

| CN | 202683225 | 1/2013 |
| KR | 1020090090194 | 8/2009 |
| KR | 1020090121447 | 11/2009 |
| KR | 1020130057269 | 5/2013 |

OTHER PUBLICATIONS

PCT/ISA/237 Written Opinion issued on PCT/KR2018/008679, pp. 7. (dated Mar. 13, 2019).

Kim, Hwajin et al., "Effects of surface fluorination of TiO2 on photocatalytic oxidation of gaseous acetaldehyde", Applied Catalysis B: Environmental 69 (2007) 127-132.

Weon, Seunghyun et al., "Dual-components modified TiO2 with Pt and fluoride as deactivation resistant photocatalyst for the degradation of volatile organic compound", Applied Catalysis B: Environmental 220 (2018) 1-8.

Weon, Seunghyun et al., "Active {001} Facet Exposed TiO2 Nanotubes Photocatalyst Filter for Volatile Organic Compounds Removal: From Material Development to Commercial Indoor Air Cleaner Application", Environ. Sci. Technol. 2018, 52, 9330-9340, pp. 11.

Ong, Wee-Jun et al., "Highly reactive {001} facets of TiO2-based composites: synthesis, formation mechanism and characterization", Nanoscale, 2014, 6, 1946, pp. 63.

Korean Office Action dated Jul. 7, 2022 issued in counterpart application No. 10-2018-0002699, 10 pages.

Guiying Li et al., "Enhanced Simultaneous PEC Eradication of Bacteria and Antibiotics by Facilely Fabricated High-Activity {001} facets TiO2 mounted onto TiO2 nanotubular Photoanode", Water Research, 2016, 9 pages.

Korean Office Action dated Nov. 23, 2022 issued in counterpart application No. 10-2018-0002699, 3 pages.

METHOD FOR MANUFACTURING PHOTOCATALYTIC FILTER FOR AIR PURIFICATION

PRIORITY

This application is a National Phase Entry of International Application No. PCT/KR2018/008679, which was filed on Jul. 31, 2018, and claims priority to Korean Patent Application No. 10-2018-0002699, which was filed in the Korean Intellectual Property Office on Jan. 9, 2018, the content of each of which is incorporated herein by reference.

TECHNICAL FIELD

The present disclosure relates to a method for manufacturing a photocatalytic filter for air purification, and more specifically to a method for manufacturing a photocatalytic filter for air purification that changes a titanium dioxide surface crystal structure used as a photocatalyst to improve photocatalytic activity.

BACKGROUND ART

Recently, as the demand for air purifying devices for purifying indoor air is increased due to air pollution, fine dust, yellow-dust, and the like, air purifying devices of various methods have been produced. For example, there have been air purifying devices using filters in a nonwoven fabric form and air purifying devices using electrostatic filters of an electrostatic precipitating method. However, although filtering dust with these filters has been possible, removing odor or sterilizing bacteria has been difficult. Accordingly, a separate deodorizing filter made of activated carbon has been used for deodorization, but there have been problems such as a deodorizing filter using activated carbon having poor durability and not being able to sterilize harmful microorganisms included in the air.

In order to solve these problems, technologies using photocatalytic material capable of performing air purifying functions such as deodorization and sterilization are being researched, and titanium dioxide (TiO2) may be identified as the leading photocatalytic material. Titanium dioxide generates radicals when subject to ultraviolet rays, which may sterilize microorganisms as well as degrade odorous substances that cause odors by the strong oxidizing power of the radicals.

In order to use photocatalytic materials as described above, a separate light source such as a light emitting diode (LED) needs to be provided in an air purifying device. Although, air purifying effect may be increased with more light sources increasing photocatalytic reaction, there is the disadvantage of energy consumption increasing relatively.

Accordingly, there is a need for an air purifying device applied with a photocatalyst capable of reducing energy consumption while improving air purifying effect.

DISCLOSURE

Technical Problem

The present disclosure is in accordance with the above-described needs, and an object of the disclosure is in providing a method for manufacturing photocatalytic filter for air purification that changes a titanium dioxide surface crystal structure used as a photocatalyst to improve photocatalytic activity.

Technical Solution

According to an embodiment, a method for manufacturing a photocatalytic filter for air purification method includes obtaining a nanostructured titanium dioxide ($TiO_2$) by oxidizing a titanium metal, immersing the nanostructured titanium dioxide in an acidic fluorine-containing solution and reacting for a predetermined period of time, and after treatment in the acidic fluorine-containing solution, performing annealing on the nanostructured titanium dioxide.

The acidic fluorine-containing solution may be 3 pH to 4 pH.

The acidic fluorine-containing solution may be 3.5 pH.

The acidic fluorine-containing solution may be a sodium fluoride (NaF) aqueous solution, a hydrogen fluoride (HF) aqueous solution, a lithium fluoride (LiF) aqueous solution, or a potassium fluoride (KF) aqueous solution.

The acidic fluorine-containing solution may be a NaF aqueous solution.

The predetermined period of time may be 30 minutes to 1 hour.

The manufacturing method according to the embodiment may further include manufacturing a photocatalytic filter using the obtained nanostructured titanium dioxide as material after the annealing.

The titanium metal may be in a mesh form, and a mesh formed with the nanostructured titanium dioxide obtained after the annealing may be used as a photocatalytic filter.

DETAILED DESCRIPTION OF EXEMPLARY EMBODIMENTS

Figure 1:
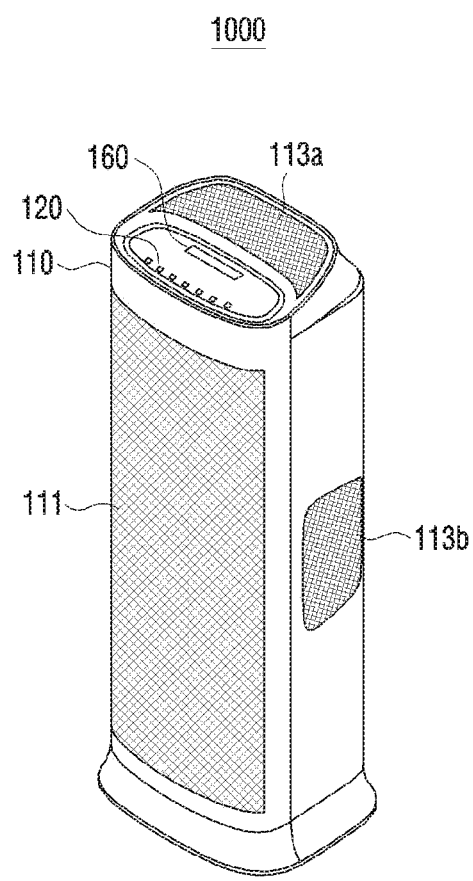
FIG. 1 is a diagram illustrating an air purifying device according to an embodiment of the disclosure.

In describing the disclosure, if a detailed description of a known function or configuration is determined as unnecessarily obscuring the gist of the disclosure, the detailed description thereof may be omitted. Further, terms used herein may be terms defined in consideration of the functions in the disclosure, and may be varied according to the intention or relationship of a user or an operator. Accordingly, the definition should be made based on the content throughout the disclosure.

Terms such as "first" and "second" may be used to describe a variety of elements, but the elements should not be limited by these terms. The terms are used only for the purpose of distinguishing one element from another.

The terms used herein are used only to describe a specific embodiment, and not intend to limit the scope of the claims. A singular expression may include a plural expression, unless otherwise specified. It is to be understood that the terms such as "comprise" or "consist of" are used herein to designate a presence of a characteristic, number, step, operation, element, component, or a combination thereof, and not to preclude a presence or a possibility of adding one or more other characteristics, numbers, steps, operations, elements, components or a combination thereof.

The terms used herein are used only to describe a specific embodiment, and should not be construed as limiting the scope of other embodiments. A singular expression may include a plural expression, unless otherwise specified. The terms used herein, including technical or scientific terms, should be understood as having the same meaning as the terms commonly understood by one of ordinary skill in the art in the technical field disclosed in the disclosure. The terms defined in common dictionaries from the terms used herein may be construed to a same or similar meaning as with the meanings in the context of the related art, and should not be construed as having ideal or overly formal meanings uncles expressly defined in the disclosure. Depending on circumstances, even if a term is defined in the disclosure, the term may not be interpreted as excluding the embodiments disclosed herein.

Embodiments of the disclosure will be described in greater detail below assisting the understanding of one of ordinary skill in the art to which the disclosure pertains. However, the disclosure may be embodied in various different forms, and is not limited to the embodiments described herein. In the drawings, parts unrelated to the description have been omitted for clarity, and like reference numerals have been affixed to like parts throughout the specification.

The disclosure relates to a filter used in an air purifying device (or air purifier). The air purifying device, as a device for purifying indoor air of a building, may be a device with a built-in fan that is mainly installed in households, offices, and the like and used for collecting dust floating in air or removing gas in parallel therewith. The air purifying device may refer to all devices provided with a function for purifying air. For example, the air purifying device may be implemented as a device for purifying purposes only or as a device capable of performing multi-functions such as an air conditioner equipped with air purifying function, a humidifier equipped with air purifying function, and the like.

FIG. 1 is a diagram illustrating an air purifying device according to an embodiment of the disclosure. Referring to FIG. 1, the air purifying device 1000 may include a main body 110 forming an exterior, a suction port 111 for suctioning air from an indoor space, discharge ports 113a and 113b through which air that is introduced and purified may be discharged, an inputter 120, and a display 160 for displaying an operating state of the air purifying device 1000.

The inputter 120 may include a button for inputting various control information related to the air purifying device 1000 such as a power button for turning on or turning off power in the air purifying device 1000, a timer button for setting a driving time of the air purifying device 1000, a lock button for limiting operation by the inputter to prevent accidental operation of the inputter, and the like. Each input button may be a push switch and a membrane switch, which is a method of generating an input signal through pressing by a user, or a touch switch, which generates an input signal through touching by a body part of the user.

If the inputter 120 adopts the touch switch method, the inputter 120 may be implemented as an integrated type with the display 160.

The display 160 may display information on a state of the air purifying device 1000. For example, information on the degree of contamination of a filter within the air purifying device 1000, information on the filter exchange period, and information currently in progress activity (e.g., information on whether the stage is air quality sensing stage or filtering stage, information on air flow direction, etc.) may be displayed. According to another embodiment, information such as the above may be provided to an external device such as a smartphone that communicates with the air purifying device 1000.

Figure 2:
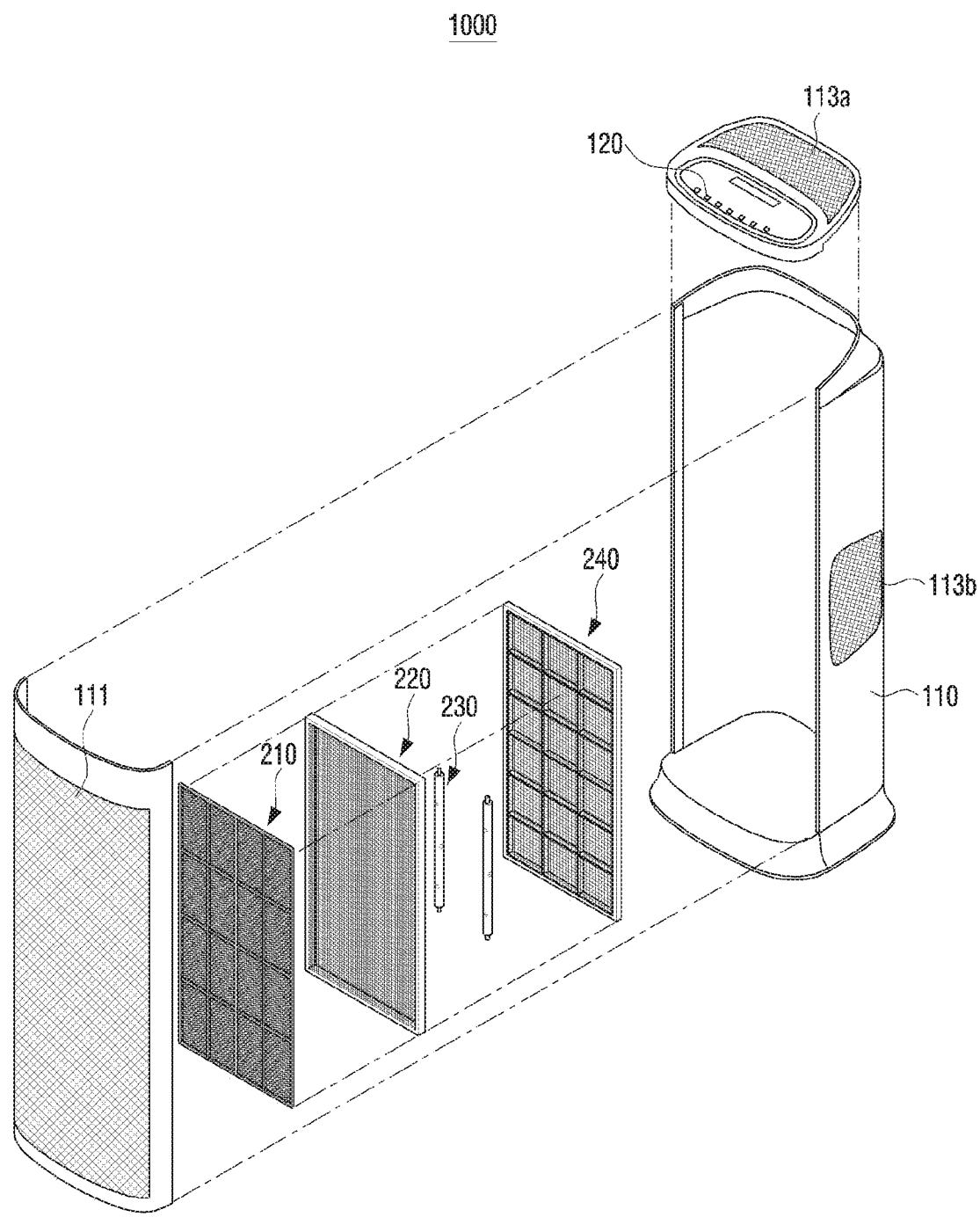
FIG. 2 is a diagram illustrating an interior configuration of an air purifying device according to an embodiment of the disclosure.

FIG. 2 is a schematic exploded perspective diagram of an air purifying device 1000 according to an embodiment of the disclosure.

Referring to FIG. 2, the air purifying device 1000 may include a pre-filter 210, a high-efficiency particulate air (HEPA) filter 220, a light source 230, and a photocatalytic filter 240 within a main body 110. Although not illustrated, a deodorizing filter including activated carbon may be further included between the pre-filter 210 and the HEPA filter 220. The arrangement order of the filters may be as illustrated in FIG. 2, or arranged in different order. In addition, the number of filters may also not be limited as illustrated in FIG. 2. Some of the configurations may be omitted according to the embodiments, and although not illustrated, configurations obvious to those skilled in the art may be further included in the air purifying device 1000.

Although not illustrated, the air purifying device 1000 may include at least one fan for introducing air that is circulated in an indoor space into the main body 110 through a suction port 111. The air introduced through the suction port 111 may pass through the filters, and impurities in air are filtered.

In the pre-filter 210, comparatively large dust particles may be primarily filtered. The HEPA filter 220 may be configured to filter fine dust and the like that has not been previously filtered, and may be composed of, for example, glass fiber.

The light source 230 may emit light in a light source appropriate for generating a photocatalytic reaction in a photocatalyst consisting the photocatalytic filter 240. For example, the light source 230 may be implemented as a device such as a fluorescent lamp and an incandescent lamp or a light emitting diode (LED), and may emit light having a wavelength range of a white light, a red light, a green light, a blue light, ultraviolet rays, visible rays, infrared rays, near infrared (NIR; 0.75 µm to 1.4 µm), short wave infrared (SWIR; 1.4 µm to 3 m), mid wave infrared (MWIR; 3 µm to 8 µm), long wave infrared (LWIR; 8 µm to 15 µm), far infrared (FIR; 15 µm to 1000 µm), and the like.

In FIG. 2, although the light source 230 may be illustrated as disposed on one side of the photocatalytic filter 240, the light source is not always limited to the arrangement form, and may be provided on each of the both sides of the photocatalytic filter 240. In addition, the light source 230 may not necessarily be disposed to face the photocatalytic filter 240, but may be disposed at any position appropriate for emitting light to the photocatalytic filter 240.

The photocatalytic filter 240 may induce a chemical reaction by light energy to sterilize various pathogens and bacteria present in air, may remove harmful substances such as nitrogen oxides ($NO_x$), sulfur oxides ($SO_x$), and formaldehyde in air, may decompose odorous substances such as acetaldehyde, ammonia, and hydrogen sulfide, and may decompose organic materials such as tobacco smoke and oil residues. In addition, the photocatalytic filter 240 may not only remove gas, but also remove dust and the like by charging generated photoelectrons.

Materials that assist an initial inducement of the reaction may be referred to as a photocatalyst, and the photocatalytic filter 240 may use titanium dioxide (TiO2), silicon dioxide ($SiO_2$), vanadium oxide ($V_2O_3$), zinc oxide (ZnO), zirconium oxide ($ZrO_2$), cadmium sulfide (CdS), tungsten oxide ($WO_3$), and the like as a photocatalyst.

According to an embodiment, the photocatalytic filter may use titanium dioxide (TiO2) as a photocatalytic material.

When titanium dioxide (TiO2) is subject to light, electrons (e−) and holes (h+) may be generated, and electrons (e−) may react with surface absorbed oxygen to produce superoxide anion ($O_2$−) and holes (h+) may produce hydroxide (OH Radical) with a strong oxidization function. Based on the oxidization, effects of anti-fouling, anti-bacterial, sterilization, deodorization, removal of harmful substances, reduction of air pollutants, superhydrophilicity, and the like may be generated.

Titanium dioxide (TiO2) may be composed of three crystal structures, that is {001}, {101}, and {100} facets. Because oxidation is most actively generated in {001} facet, which exhibits the highest surface energy among the facets, the amount of OH radicals generated in photocatalytic material copious in {001} facet is high, and accordingly air purification performance may also be enhanced. However, because naturally formed titanium dioxide (TiO2) has a slow growth rate along a [101] direction rather than a [001] direction, titanium dioxide (TiO2) may mostly be composed of the {001} facet, which is thermodynamically stable. The harmful gas decomposition activity of the {101} facet and the {001} facet may differ by up to eight folds.

If a photocatalyst is produced with nanostructure, a surface area may be increased and photocatalytic activity may be improved.

Accordingly, the disclosure is directed to providing a filter for air purification using a titanium dioxide (TiO2) photocatalyst, which is a nanostructure and contains the {001} facet copiously.

Figure 3:
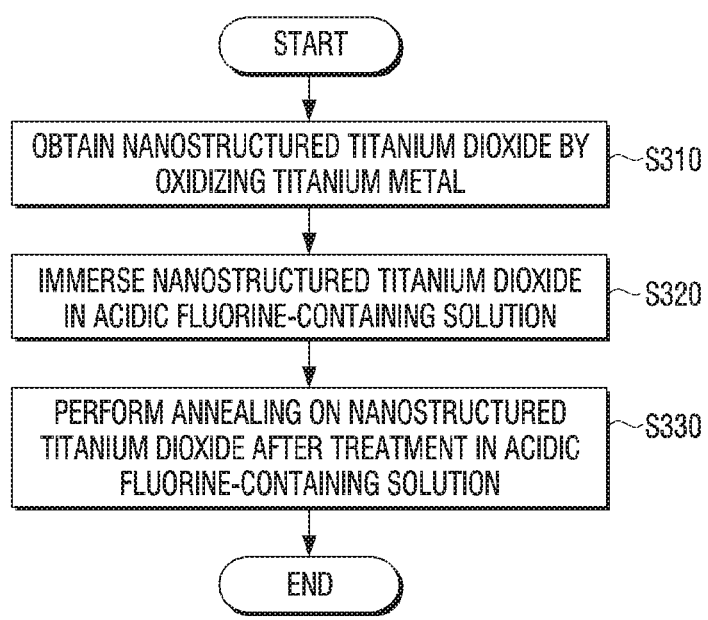
FIG. 3 is a flowchart illustrating a method for manufacturing a photocatalytic filter for air purification according to an embodiment of the disclosure.

FIG. 3 is a flowchart illustrating a method for manufacturing a photocatalytic filter according to an embodiment of the disclosure.

Referring to FIG. 3, the titanium metal may first be oxidized to obtain a nanostructured titanium dioxide (TiO2) (S310).

The form of the titanium metal used at this time may be foil, mesh, fiber, film, sheet, or the like.

The nanostructure formed by the oxidization of the titanium metal may be in the form of a nanotube, a nanocrystal, a nanofiber, a nanosheet, a nanoflower, or the like.

The obtained nanostructured titanium dioxide (TiO2) may be immersed in an acidic fluorine-containing solution and reacted during a predetermined period of time (S320). The surface of the nanostructured titanium dioxide (TiO2) may be converted to the {001} facet in this process.

The acidic fluorine-containing solution may be an aqueous solution of sodium fluoride (NaF), hydrogen fluoride (HF), lithium fluoride (LiF), potassium fluoride (KF), and the like. Preferably, the NaF aqueous solution may be used as the acidic fluorine-containing solution.

Further, the power of hydrogen (pH) of the acidic fluorine-containing solution may be between 3 and 4, and the predetermined period of time may be between 30 minutes to 1 hour. The pH may induce a sufficient reaction with only a comparatively short time by forming an acidic environment of 3 pH to 4 pH.

After treatment in the acidic fluorine-containing solution, annealing may then be performed on the nanostructured titanium dioxide (TiO2) (S330). The annealing temperature, at this time, may be 350° C. to 400° C.

According to an embodiment, the method for manufacturing a photocatalytic filter may further include an additional step of manufacturing a photocatalytic filter using the obtained nanostructured titanium dioxide as a material after the annealing. According to another embodiment, the additional step may be omitted based on using from the beginning the titanium metal manufactured in the form of the photocatalytic filter. In this case, the titanium metal in the form of the photocatalytic filter may be in, for example, mesh form.

Based on immersing the nanostructure in the acidic fluorine-containing solution and annealing at high temperature thereafter as described in the manufacturing method above, a nanostructured titanium dioxide with copious {001} facet may be obtained. Accordingly, photocatalytic activity of the photocatalytic filter may be enhanced.

Figure 4:
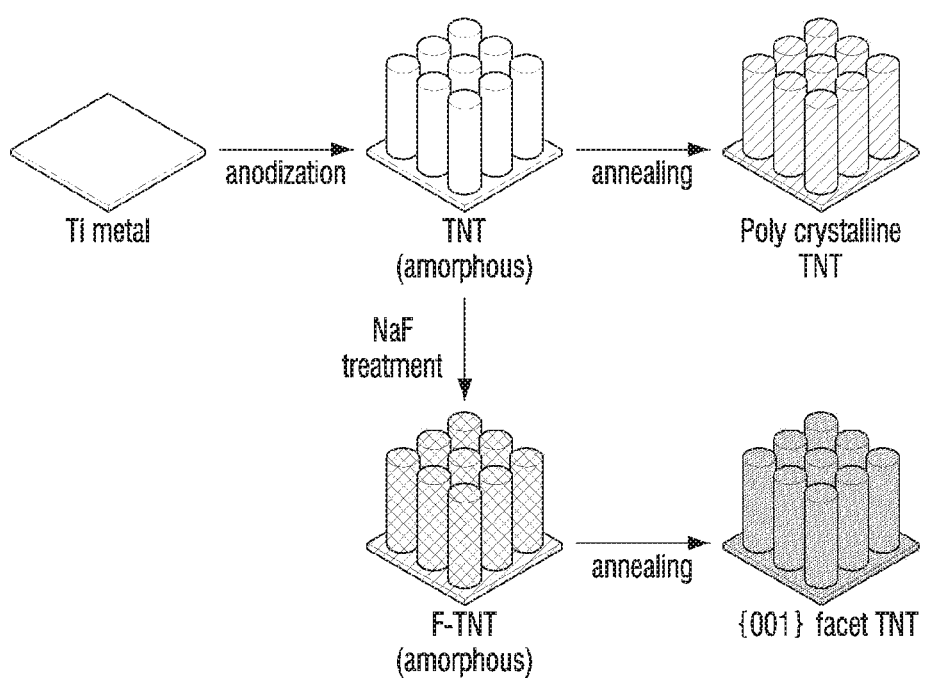
FIG. 4 is a diagram illustrating a comparison of a nanostructure that has undergone a process of reacting in a fluorine-containing solution (NaF), and a nanostructure that has not undergone a process of reacting in a fluorine-containing solution according to an embodiment of the disclosure.

FIG. 4 is a diagram illustrating a comparison of a nanostructure that has undergone a process of reacting in a fluorine-containing solution (NaF), and a nanostructure that has not undergone a process of reacting in a fluorine-containing solution according to an embodiment of the disclosure. Referring to FIG. 4, an amorphous titanium dioxide nanotube ($TiO_2$ Nanotube; TNT) may be obtained by oxidizing titanium metal, and a polycrystalline TNT with mostly {101} facet may be formed after annealing. Alternatively, based on performing the process of reacting the amorphous titanium dioxide nanotube in a fluorine-containing solution, an amorphous titanium dioxide nanotube (F-TNT) containing fluorine on the surface may be obtained, and the titanium dioxide nanotube ({001} facet TNT) containing {001} facet copiously may be formed when annealing is performed thereafter. In case the process of reacting in fluorine-containing solution is not performed, there may be no change to the color of the nanotube, but in case the process of reacting in fluorine-containing solution is performed, whether a nanotube is formed or whether a defect is manufactured from the manufacturing process may be identified by color change since the nanotube changes in color from black to dark brown.

A method of manufacturing a photocatalytic filter according to an embodiment will be described below to assist in the understanding of the disclosure. The embodiment below is merely one embodiment of the disclosure, and the disclosure is not limited to the following embodiment.

Manufacturing Embodiment of a Photocatalytic Filter

The method of manufacturing a photocatalytic filter according to an embodiment of the disclosure may perform anodization, NaF treatment, and annealing process as follows.

1. Anodization
  1) Cut titanium foil or mesh to a desired size.
  2) Sonicate for 10 minutes in acetone, ethanol, and distilled water respectively (pre-treatment process).
  3) Perform anodization of titanium foil or mesh to a positive electrode, and platinum (Pt) to a negative electrode at 50 V for 1 hour. At this time, an ethylene glycol electrolyte of 0.2 wt % ammonium fluoride (NH4F), and 1 vol % water (H2O) may be used as an anodization solution.

4) An amorphous titanium dioxide nanotube (amorphous TiO2 nanotube) may be formed as a result of oxidation.

2. NaF Treatment

1) Prepare an NaF aqueous solution (NaF: 30 mM, pH 3.5).

2) Immerse the amorphous titanium dioxide nanotube prepared by anodization in the NaF aqueous solution to react for 30 minutes.

3) The amorphous titanium dioxide nanotube may change to black through reaction with F− ions (surface crystal structure transformation).

3. Annealing

1) Perform annealing at 400° C. for 3 hours.

2) Based on annealing, a titanium dioxide nanotube with an exposed dark brown {001} facet may be formed.

Comparative Manufacturing Example of a Photocatalytic Filter

Compared to the method of manufacturing according to the above-described embodiment, NAF treatment has not been performed in the method of manufacturing according to a comparative example. Specifically, the method is comprised of anodization and annealing process as follows.

1. Anodization

1) Cut titanium foil or mesh to a desired size.

2) Sonicate for 10 minutes in acetone, ethanol, and distilled water respectively (pre-treatment process).

3) Perform anodization of titanium foil or mesh to a positive electrode, and platinum (Pt) to a negative electrode at 50 V for 1 hour. At this time, an ethylene glycol electrolyte of 0.2 wt % ammonium fluoride (NH4F), and 1 vol % water (H2O) may be used as an anodization solution.

4) An amorphous titanium dioxide nanotube (amorphous TiO2 nanotube) may be formed as a result of oxidation.

2. Annealing

Perform annealing on the formed amorphous titanium dioxide nanotube at 400° C. for 3 hours.

Figure 5:
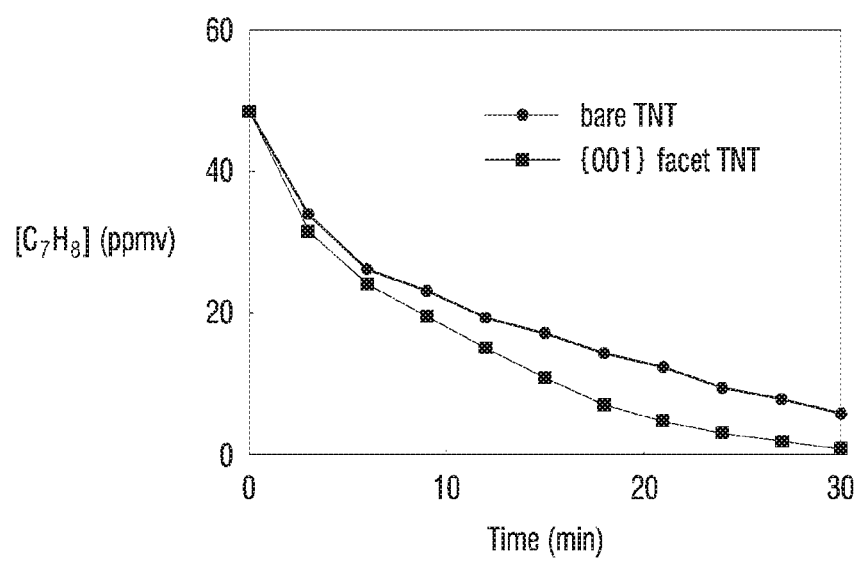
FIGS. 5 to 6 are diagrams illustrating a comparison of a photocatalytic activity of a filter according to an embodiment of the disclosure and a photocatalytic activity of a filter according to a comparative example.
Figure 6:
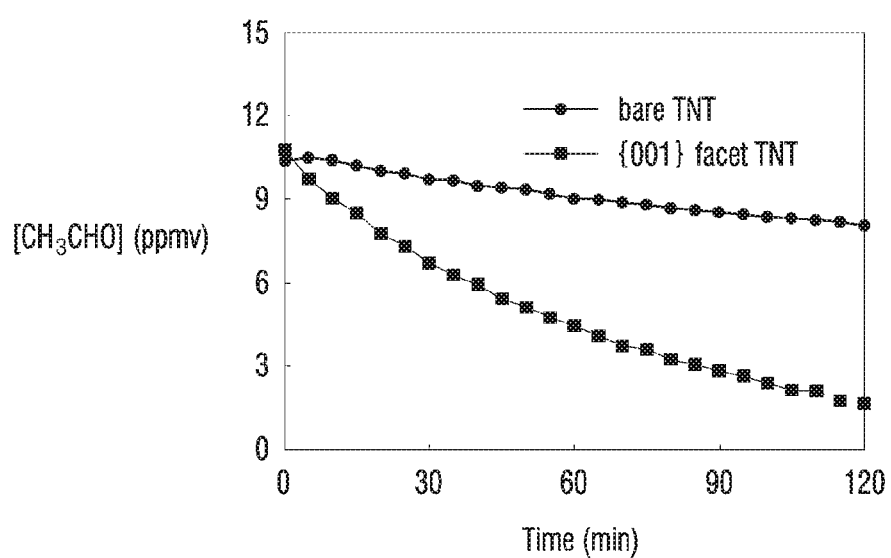

FIGS. 5 to 6 are diagrams illustrating a comparison of a photocatalytic activity of a filter manufactured according to an embodiment of the disclosure and a photocatalytic activity of a filter manufactured according to a comparative example described above.

FIG. 5 is a graph illustrating a toluene gas decomposition performance based on reaction to ultraviolet rays on titanium dioxide nanotube ({001} facet TNT) containing {001} facet copiously by performing the processing of reacting the photocatalytic filter (bare TNT) manufactured according to the comparative example and the fluorine-containing solution according to an embodiment of the disclosure.

The toluene gas decomposition performance showed greater superiority when reacted with ultraviolet rays (365 nm) in the case of titanium dioxide nanotube ({001} facet TNT) that performed the process of reacting with the fluorine-containing solution according to an embodiment of the disclosure compared to the photocatalytic filter (bare TNT) manufactured according to the comparative example.

FIG. 6 is a graph illustrating an acetaldehyde gas decomposition performance based on reaction to visible rays on titanium dioxide nanotube ({001} facet TNT) containing {001} facet copiously by performing the processing of reacting the photocatalytic filter (bare TNT) manufactured according to the comparative example and the fluorine-containing solution according to an embodiment of the disclosure.

In the case of the photocatalytic filter (bare TNT) manufactured according to the comparative example, the acetaldehyde gas was hardly decomposed when reacted to visible rays (wavelength>420 nm), but in the case of titanium dioxide nanotube ({001} facet TNT) that performed the process of reacting with the fluorine-containing solution according to an embodiment of the disclosure, the acetaldehyde gas was decomposed when reacted to visible rays. That is, because the photocatalytic filter manufactured according to an embodiment of the disclosure may react to not only ultraviolet rays but also visible rays, using general fluorescent lamps may be possible.

In the method of forming titanium dioxide of a crystal structure through a conventional hydrothermal method, strong pressure, high temperature, and long reaction time (12 hours or more) was required. The method may be applicable when manufacturing titanium dioxide powder, but may not be applicable to nanostructured titanium dioxide because the nanostructure may be destroyed by high temperature and high pressure. On the other hand, according to a manufacturing method according to an embodiment, because a {001} crystal structure may be formed even though high temperature and high pressure is not applied for a long period of time, it may be applicable to the nanostructured titanium dioxide.

In addition, the photoactivity of the filter having the nanostructured titanium dioxide according to an embodiment on the surface may be higher than that of the filter having the surface coated with conventional titanium dioxide powder on the substrate.

Because the titanium dioxide nanostructure formed through anodization is mostly {101} facet, there may be difficulty in securing sufficient harmful gas decomposition performance. On the other hand, because the photocatalytic filter according to an embodiment contains {101} facet with high photoactivity copiously by fluorine treating an anodized titanium dioxide nanostructure, sufficient harmful gas removal performance may be exhibited.

In addition, the photocatalytic filter of the disclosure may be advantageous in exhibiting sufficient photocatalytic activity under not only ultraviolet rays but also under visible rays. That is, since photocatalytic reaction may be possible with even little light energy, the cost and energy consumption in system configuration may be reduced.

Although the photocatalytic filter has been described as being used in an air purification device above, the photocatalytic filter manufactured according to the embodiments is capable of performing an anti-bacterial function, an air purifying function, a deodorizing function, an anti-fouling function, and a water purifying function using the photocatalyst material, and thus may be utilized in various fields. For example, the photocatalytic filter may be disposed in a refrigerator, a kimchi refrigerator, a closet, a shoe closet, a washer, a septic tank, a sterilizer, a humidifier, a cleaner, an air-conditioner, and the like to perform the function of removing odor, purifying water, removing bacteria, purifying indoor air, and the like. In addition, the photocatalytic filter may be used in small products such as, for example, a smartphone, a tablet personal computer (PC), smart watch patch, or in other produces (e.g., gloves, bands, necklaces, bracelets, rings, headbands, earphones, earrings, clothing, etc.). Further, the photocatalytic filter may also be utilized in window frames, wall paper, construction, air-conditioning systems, bathroom tiles, and the like.

While the exemplary embodiments of the disclosure have been illustrated and described, the disclosure is not limited to the above-described specific embodiments, and it will be understood by those of ordinary skill in the art that various changes in form and details may be made therein without departing from the spirit and scope as defined, and these changes in form and details are not be understood as individual from the technical idea or scope of the disclosure.

What is claimed is:

1. A method for manufacturing a photocatalytic filter for air purification method, the method comprising:
   obtaining a nanostructured titanium dioxide ($TiO_2$) by oxidizing a titanium metal;
   immersing the nanostructured titanium dioxide in an acidic fluorine-containing solution and reacting for a predetermined period of time; and
   after treatment in the acidic fluorine-containing solution, performing annealing on the nanostructured titanium dioxide at a temperature substantially between 350° C. to 400° C.,
   wherein when the reacting and the annealing to the titanium dioxide are performed, the titanium dioxide includes more {001} facets than {101} facets and {100} facets.

2. The method of claim 1, wherein the acidic fluorine-containing solution is 3 pH to 4 pH.

3. The method of claim 1, wherein the acidic fluorine-containing solution is 3.5 pH.

4. The method of claim 1, wherein the acidic fluorine-containing solution is a sodium fluoride (NaF) aqueous solution, a hydrogen fluoride (HF) aqueous solution, a lithium fluoride (LiF) aqueous solution, or a potassium fluoride (KF) aqueous solution.

5. The method of claim 1, wherein the acidic fluorine-containing solution is a NaF aqueous solution.

6. The method of claim 1, wherein the predetermined period of time is 30 minutes to 1 hour.

7. The method of claim 1, further comprising:
   manufacturing a photocatalytic filter using the obtained nanostructured titanium dioxide as material after the annealing.

8. The method of claim 1, wherein the titanium metal is in a mesh form, and a mesh formed with the nanostructured titanium dioxide obtained after the annealing is used as a photocatalytic filter.

* * * * *